(12) United States Patent
Kostopoulos

(10) Patent No.: US 12,029,899 B1
(45) Date of Patent: Jul. 9, 2024

(54) WRIST-WORN INDEPENDENT 3-POINT ACUPUNCTURE STIMULATOR

(71) Applicant: Larry Kostopoulos, Totonto (CA)

(72) Inventor: Larry Kostopoulos, Totonto (CA)

(*) Notice: Subject to any disclaimer, the term of this patent is extended or adjusted under 35 U.S.C. 154(b) by 0 days.

(21) Appl. No.: 17/849,767

(22) Filed: Jun. 27, 2022

(51) Int. Cl.
*A61N 1/18* (2006.01)
*A61N 1/22* (2006.01)

(52) U.S. Cl.
CPC ..................... *A61N 1/22* (2013.01)

(58) Field of Classification Search
CPC .................... A61N 1/20; A61N 1/22
See application file for complete search history.

(56) References Cited

U.S. PATENT DOCUMENTS

| | | | |
|---|---|---|---|
| 11,478,606 B1* | 10/2022 | English | A61M 21/02 |
| 2006/0041283 A1* | 2/2006 | Gelfand | A61N 1/36114 607/44 |
| 2009/0228084 A1* | 9/2009 | Chen | A61N 1/40 607/115 |
| 2014/0188025 A1* | 7/2014 | Aziz | A61F 5/0106 602/5 |
| 2015/0045693 A1* | 2/2015 | Otsamo | A61B 5/1104 600/554 |
| 2016/0045739 A1* | 2/2016 | Rezai | A61N 1/36096 607/45 |
| 2022/0054856 A1* | 2/2022 | Wang | A61N 1/36025 |
| 2022/0331582 A1* | 10/2022 | Kim | A61B 5/4812 |

FOREIGN PATENT DOCUMENTS

KR 20120007148 U * 10/2012

OTHER PUBLICATIONS

English translation of KR 20120007148 published Oct. 12, 2012 (Year: 2012).*

* cited by examiner

*Primary Examiner* — Allen Porter
*Assistant Examiner* — Adreanne A. Arnold
(74) *Attorney, Agent, or Firm* — Heer Law; Stephano Salani

(57) ABSTRACT

A method and device for controlling nausea, anxiety and stress. The device includes a wristwatch-like housing, electrical circuitry for generating electrical impulses of which low-frequency of which direct current (DC) electrical pulses are preferred, a metal ground plate, three adjustable metal contact points, indicator lights, function buttons on the housing, and a strap for securing the housing to the wrist. There may also be a screen display for visualizations of different functions. An internal processor controls all device functions and can optionally communicate via USB or short-range communications with a telephone App. The method allows simultaneous application of a pulse voltage output to acupuncture points H7, Lu9 and P6 (Buddha's Triangle). An alternate embodiment uses three permanent magnets to simultaneously stimulate the three points of Buddha's Triangle.

18 Claims, 7 Drawing Sheets

WRIST-WORN INDEPENDENT 3-POINT ACUPUNCTURE STIMULATOR

BACKGROUND

Field of the Invention

The present invention relates generally to the field of wrist-worn equipment, and more particularly to a wrist-worn device that can independently stimulate any one, any two or all three acupuncture points P6, H7 and Lu9.

Description of the Problem Solved

Nausea, anxiety and stress are three common problems that numerous people experience or suffer from. It is well-known in the art of acupuncture that there are three acupuncture points on the palmar (inside) side of the wrist. These three points are called Buddha's Triangle, and consist of point P6 or Pericardium 6, H7 or Heart 7 (sometimes HT7), and Lung 9 (Lu9).

Stimulating point P6 helps unbind the chest, regulate the heart and calm the mind; it is also very effective in combating nausea and vomiting.

Stimulating point H7 helps to calm the mind as well as help with insomnia, talking during sleep, poor memory, mania-depression, dementia, sadness, fear, disorientation and grief as well as providing relief for heart-related emotional issues.

Stimulating Lu9 helps control the nervous system and relieve acute stress by helping with breathing. Shallow breathing is not just a stress response; it becomes a habit that feeds stress. Shallow breathing also lowers the amount of lymphocytes, a type of white blood cell that helps to defend the body from invading organisms as well as countless other negative health effects.

Stimulation of these acupuncture points can be accomplished by electrical pulses or currents, magnetic fields and directed light.

It would be advantageous to have a wrist-worn stimulator that could stimulate any one of these points independently or any combination of them simultaneously including all three at the same time.

SUMMARY OF THE INVENTION

The present invention relates to a method and device for controlling nausea, anxiety and stress. The device includes a wristwatch-like housing, electrical circuitry for generating electrical impulses of which low-frequency direct current (DC) electrical pulses are preferred, a metal ground plate, three adjustable metal contact points, indicator lights, function buttons on the housing, and a strap for securing the housing to the wrist. There may also be a screen display for visualizations of different functions. An internal processor controls all device functions and can optionally communicate via USB or short-range communications with a telephone App. The method allows simultaneous application of a pulse voltage output to acupuncture points H7, Lu9 and P6 as well as individual application to the points separately or in any combination. Another embodiment of the invention simply uses three permanent magnets positioned over the acupuncture points H7, Lu9 and P6 when worn.

DESCRIPTION OF THE FIGURES

Attention is now directed to several drawings that illustrate features of the present invention.

FIG. 6 is a flow chart for feedback stress turn-on.

Several figures and illustrations have been provided to aid in understanding the present invention. The scope of the present invention is not limited to what is shown in the figures.

DESCRIPTION OF THE PREFERRED EMBODIMENTS

The present invention relates to a device for controlling nausea, anxiety and stress. The device includes a wristwatch-like housing, electrical circuitry for generating electrical impulses of which low-frequency, direct current (DC) electrical impulses are preferred, a metal ground plate, three adjustable metal contact points, indicator lights, function buttons on the housing, and a strap for securing the housing to the wrist. There may also be a screen display for visualizations of different functions.

In the following description, a direct current (DC) pulse or DC square-wave pulse is a pulse whose time signature does not cross zero volts (always positive with respect to a ground reference electrode). Thus, a 1 volt DC pulse pulses from zero when low to 1 volt peak when high.

The word "approximately" in reference to any value being discussed or claimed means that the actual value (which can vary with temperature or other ambient or electronic conditions) is close to the specified value (within plus or minus 1%).

In various embodiments of the invention, stimulation may be alternatively or cumulatively produced using directed light such as that from low-level lasers or light-emitting diodes (LEDs), or by magnetic fields produced by magnets such as small electromagnets.

Feedback may be used in an open-or closed-loop control system to initiate or modulate the stimulation. For example, photoplethysmography (PPG) may be used to detect changes in heart rate (HR) and heart rate variability (HRV) which are key indicators of a person's stress level. When negative HRV changes are detected (indicating stress), the device can automatically activate for a set period of time, such as from one to five minute(s) of treatment time. While one to five minutes is preferred, any treatment time is within the scope of the present invention, and may be made adjustable.

Figure 1:
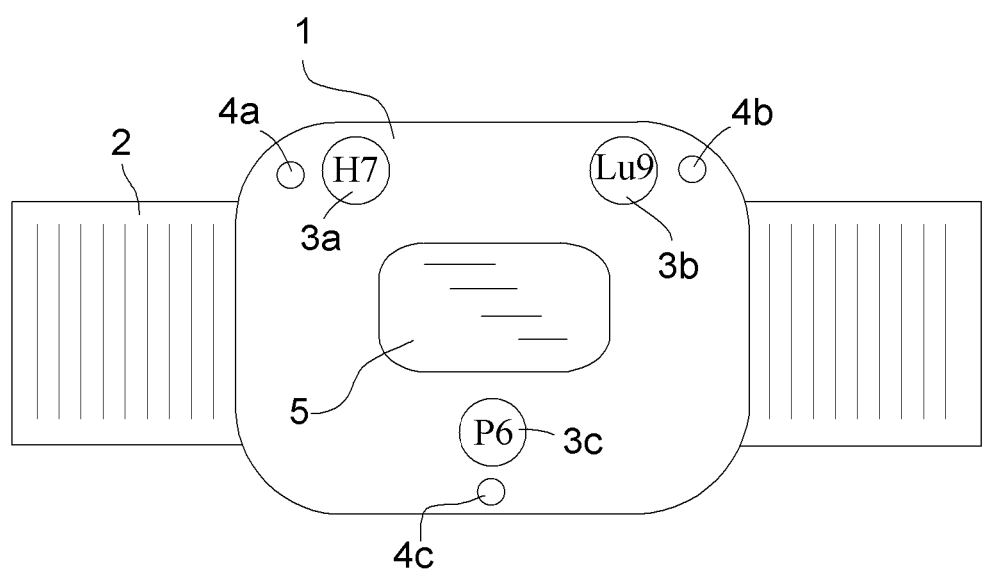
FIG. 1 shows an embodiment of the present invention that resembles a wrist-watch.

FIG. 1 shows an embodiment of the present invention. A wristwatch-like case 1 has a strap or band 2. The case in this embodiment has three buttons with indicators for the three acupuncture points. Button 3a activates stimulation to point H7 lighting indicator 4a. Button 3b activates stimulation to point LU1 lighting indicator 4b. Button 4c activates stimulation to point P6 lighting indicator 4c. The indicators 4a, 4b and 4c can be small LEDs or other types of lights. The embodiment of FIG. 1 can also be equipped with a display screen that can optionally be a touch screen. This screen can be used to select combinations of the points being stimulated, and it can be used to control the device such as setting a timer.

Figure 2A:
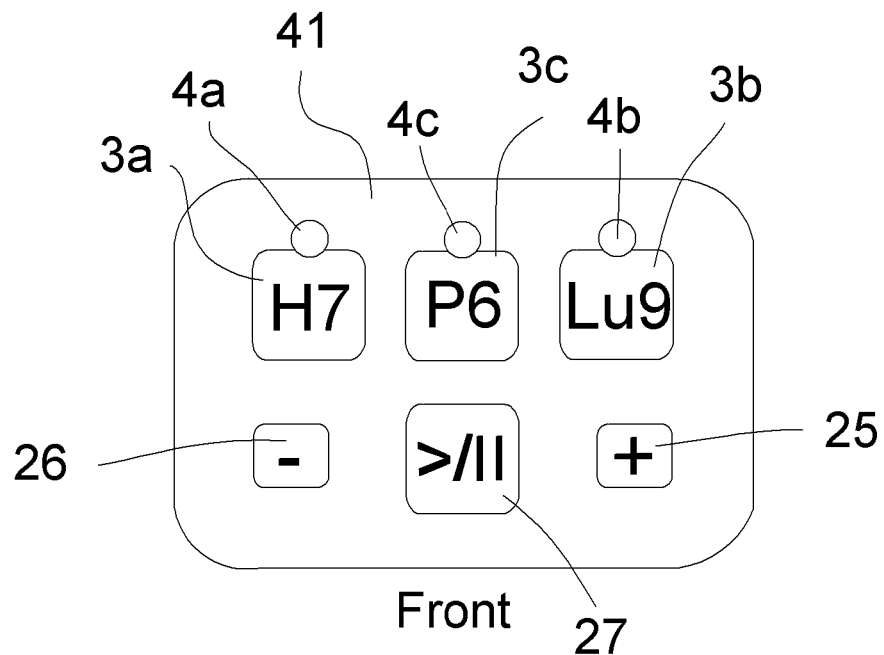
FIGS. 2A-2B show an alternate embodiment of the present invention top and bottom.

FIG. 2A shows a top view of an alternate embodiment of the device. This embodiment is an electro-stimulator supplying low-level direct current (DC) square-wave signal to the acupuncture point. The buttons 3a, 3b and 3c have been made larger and easier to read, while the indicators 4a, 4b and 4c have been moved closer to the corresponding button. The functions of these three buttons and indicators are the same as that of the embodiment of FIG. 1. There are also three additional buttons plus 25, minus 26 and play/pause/cancel 27 marked respectively+, – and >/||. Touching plus 25 or minus 26 causes the applied voltage level to be increased or decreased. Touching the play/pause/cancel button 27 starts the stimulation, pauses the stimulation, or cancels the selected stimulation. Combination of the stimulated points can be selected by touching more than one button simultaneously.

Figure 2B:
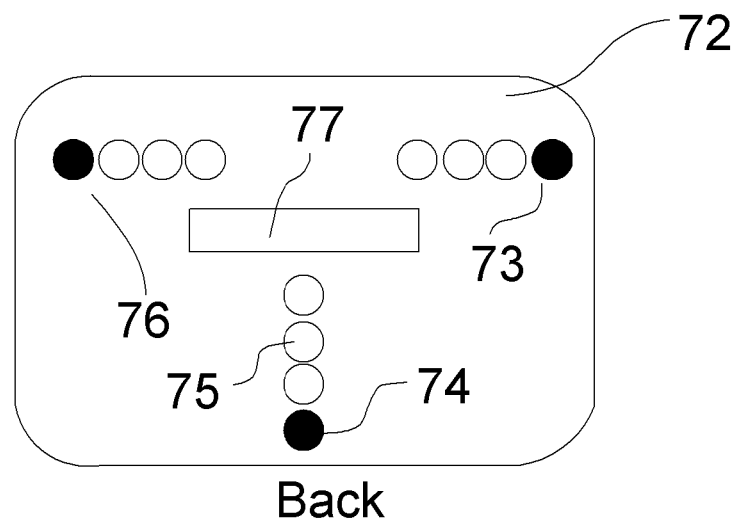

FIG. 2B shows a bottom view of the embodiment of FIG. 2A. Three electrode sets are shown 73, 74 and 76. For each electrode set, four point positions are shown. The black dot indicates the selected position, while the white (open) dots 75 are the unselected positions. Changing the selected electrode position can be done manually in some embodiments, or electronically in other embodiments using additional buttons and an optional view screen. The optional view screen allows the user to see the current test being administered, and see and adjust the selected electrode position. A return path for current or ground electrode 77 can be seen in FIG. 2B. Alternatively, the bottom surface of the device of FIG. 2B can take the form of a metal plate. The ground return electrode 77 should be positioned so that current from the activated electrode 73, 74 or 76, or combinations of them, passes through the acupuncture point.

In some embodiments of the invention, the wrist-worn device shown in FIGS. 2A-2B or FIG. 1 can communicate with a user's hand-held telephone via short-range radio (like Bluetooth™) or other short-range communication technique like magnetic induction. In this case, a complete program or App can be run on the telephone that shows the stimulation running, shows the selected electrodes, contains timers and the like and contains stored sequences of treatment for more complex application of stimulus. The touch screen on the telephone can be used to change internal parameters in the wrist-worn unit such as the location of the chosen electrode position for example.

Figure 3:
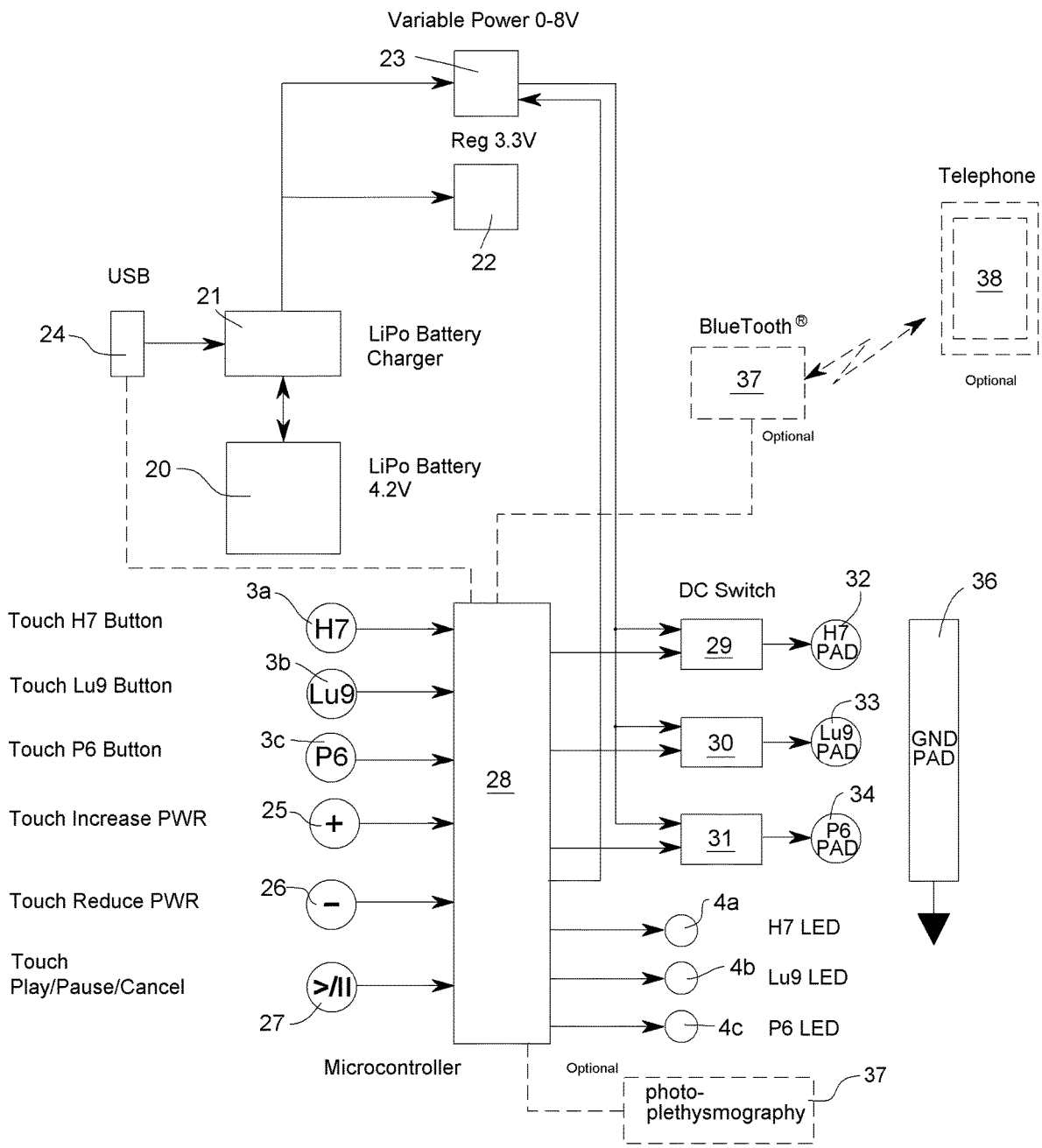
FIG. 3 is a block diagram of an electrical circuit that can independently provide electro-stimulation to one or more of the three wrist acupuncture points.

FIG. 3 shows a block diagram of the embodiment of FIGS. 2A-2B. A battery, preferably a Lithium-Polymer (LiPo) 20 supplies power for the unit. This battery typically provides 4.2 volts. Other batteries supply different voltages and are within the scope of the present invention. While a battery can be changed periodically like a watch battery, it is preferable to have one that can be recharged using methods known in the art. LiPo batteries can be recharged using a micro USB socket 24 and charging control circuitry 21.

Small micro-circuits such as microcontrollers usually run on 3.3-3.7 volts. Using a 4.2 V LiPo battery 20 thus requires a 3.3 volt regulator 22 that runs all circuitry except providing power for the actual applied pulses (normal power wiring not shown).

The applied pulses are preferably square waves of approximately 2.5 Hz with a peak voltage of between approximately 1.0 and 8.8 volts. For safety and power conservation, the pulses need to be limited to approximately 600 uA or less. While 2.5 Hz square waves are preferred, other frequencies or repetition rates and/or pulse shapes and duty cycles are within the scope of the present invention. For example, the pulse repetition rate can be between approximately 2.0 Hz and 3.0 Hz A variable power supply 23 supplies these pulses. This may be a single integrated circuit (IC) chip or discrete components. The variable power supply 23 can contain a voltage doubler circuit feeding a controllable output voltage. The voltage can be assigned by the microcontroller 28 and communicated to the variable power supply 23 by serial or parallel data or by analog voltage.

The microcontroller or micro-processor 28 can be any standard micro computing device known in art. For ease of manufacturing, the micro-controller preferably includes internal random access memory (RAM) and read-only memory (ROM). It can be mask programmed at manufacture, or it can be done with downloaded updates via the optional short-range communication 37 like Bluetooth™ or from the USB port 24. In addition to program updates, the USB port can be used to perform diagnostics and the like. The optional short-range communication 37 can be used to supply an app in the telephone 38 with system status including, but not limited to, battery charge, current pulse voltage, current pulse frequency or repetition rate, current pulse shape and the like.

The microcontroller 28 receives input from the six keys 3a, 3b, 3c, 25, 26, 27. This communication can use direct connection or a matrix type arrangement used in key pads. The microcontroller 28 can optionally communicate mono- or bi-directionally with the USB port 24 and/or the optionally short-range communication 37.

The microcontroller 28 has two sets of outputs: drives for the LEDs and on/off commands a set of switches that control the applied pulses. The LEDs 4a, 4b, 4c can be brightness modulated to indicate the applied pulse intensity (applied voltage resulting in current through the acupuncture point. The LED's are brightness modulated by allowing more or less current to flow through them. The circuitry for this may be internal to the microcontroller 28, or it may external in the form of an LED control chip (not shown).

A set of electronic switches 29, 30, 31 provide off and on control to the three acupuncture pads H7 32, Lu9 33 and P6 34. In the embodiment shown in FIG. 3, the microcontroller 28 simply turns the switches 29, 30, 31 off or on, while sending the selected voltage to the variable power supply 23.

This method is the easiest and cheapest to manufacture; however, it has the disadvantage that all electrodes being used simultaneously (such as for example H7 combined with P6) have the same voltage.

While this is normally acceptable, if, in a more complex stimulation routine, it is desired to have the different acupuncture points activated with different intensities (voltages), or even with different pulses, the variable power supply 23 can have three separate independently controllable voltage outputs, one for each electrode. The microcontroller 28, in this case can set each voltage separately at the variable power supply 23 and/or control the pulse shape with the switches 29, 30, 31. A serial message from the microcontroller 28 to the variable power supply 23 could contain three separate fields; alternatively, three outputs (wires) from the microcontroller 28 can run to the variable power supply 23.

The square wave or pulse can be generated in one of two ways: 1) it can be generated by having the microcontroller 28 simply turn the variable power supply 23 off and on, or turn the selected switch(es) 29, 30, 31 on and off at the correct frequency, or 2) the variable power supply 23 can itself contain an oscillator that produces the waveform. The easiest way is to simply have the microcontroller 28 create the waveform. This reduces the complexity of the variable power supply 23. It should be noted that all currents return to the variable power supply through the ground pad 36. Generally, this can be the same ground as the 3.3 V system ground; however, it may also be an isolated ground (ground wiring not shown in FIG. 3).

FIG. 3 also shows an optional photoplethysmography device 37 that measures the heart rate variability (HRV). This can be used for closed-loop control to be described.

Figure 4:
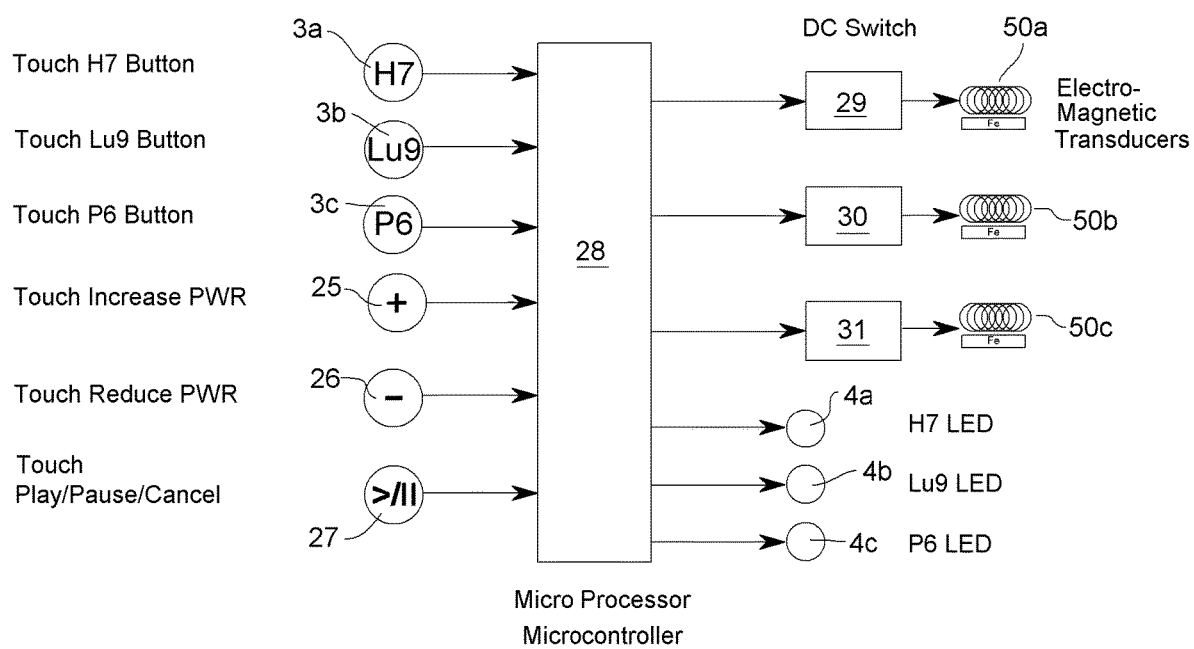
FIG. 4 shows magnetic stimulation.
Figure 5:
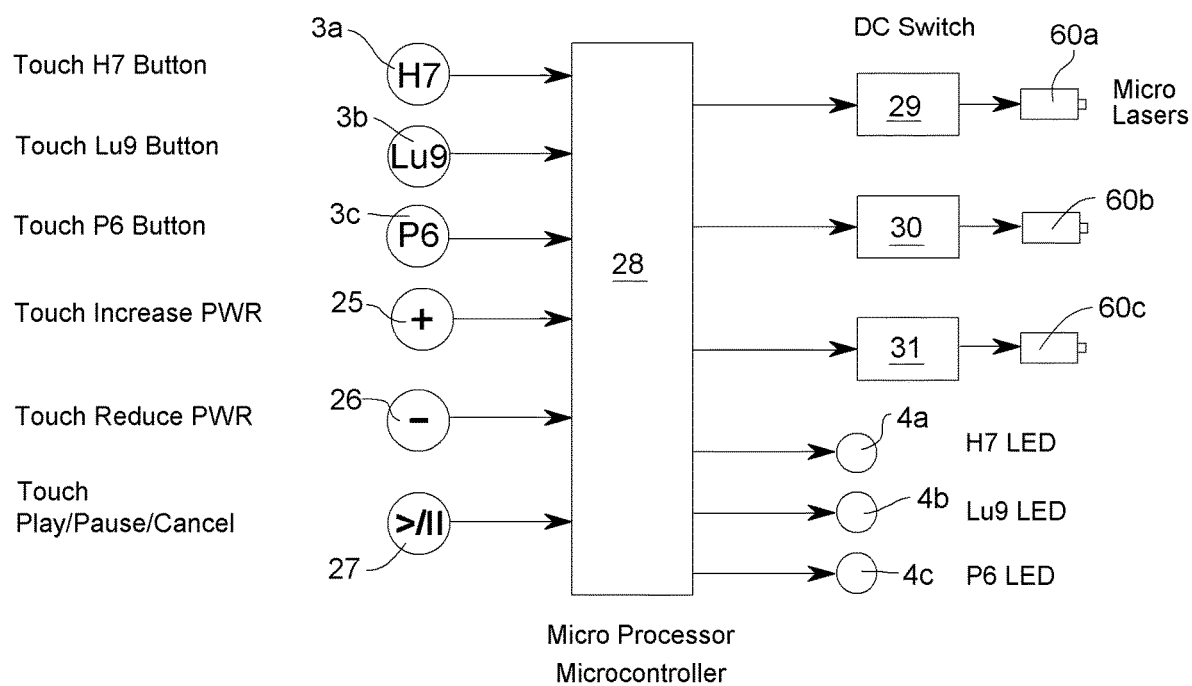
FIG. 5 shows light stimulation.

FIG. 4 shows magnetic stimulation, while FIG. 5 shows light stimulation. In FIG. 4, small electromagnetic transducer coils 50a, 50b and 50c replace the electrodes; in FIG. 5 a very small lasers or LEDs 60a, 60b and 50c replace the electrodes.

Figure 6:
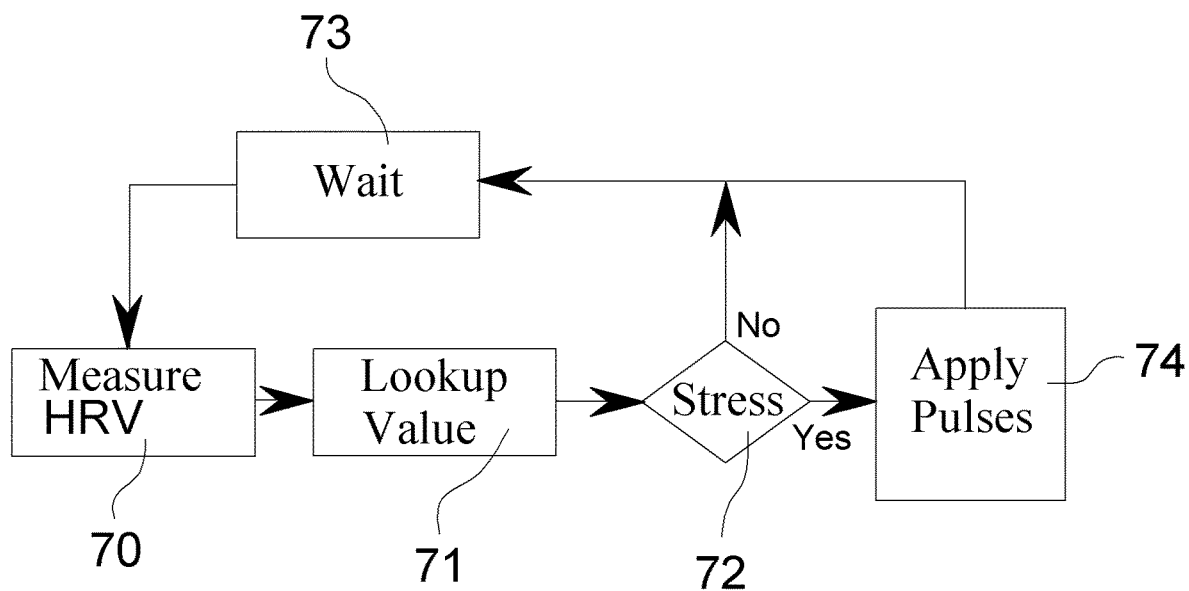

As previously stated, feedback may be used in an open-or closed-loop control system to initiate or modulate the stimulation. An example feedback loop is shown in FIG. 6. As stated, photoplethysmography (PPG) may be used to detect changes in heart rate (HR) and heart rate variability (HRV) which are key indicators of a person's stress level. The HRV (and optionally the HR) are measured 70 by the device. The HRV level is looked up 71 in a table when negative HRV changes are detected (indicating some stress). If the table indicates stress 72 the device can automatically activate for a set period of time 73, such as from one to five minute(s) of treatment time. When there is no stress, HRV can be checked again; however, a much longer wait 73 can be executed to save battery power. While one to five minutes is preferred, any treatment time is within the scope of the present invention, and may be made adjustable. Also, the table lookup 71 is optional, the device can declare stress whenever a negative HRV is measured.

Figure 7:
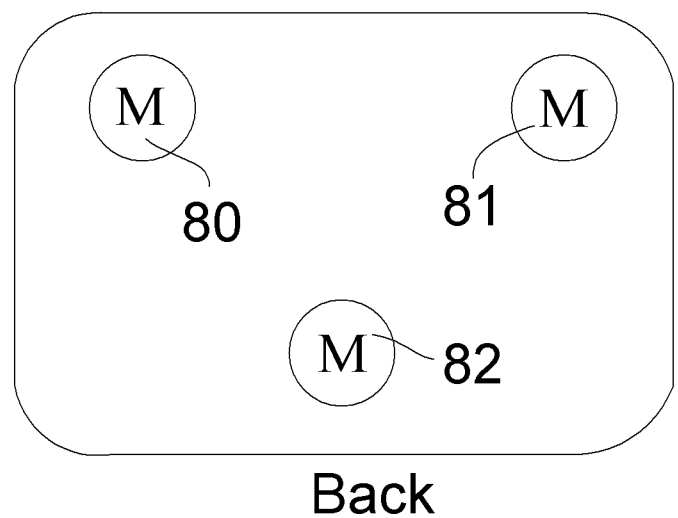
FIG. 7 shows a permanent magnet embodiment of the present invention.

An alternate embodiment shown in FIG. 7 uses three permanent magnets to simultaneously stimulate the three points of Buddha's Triangle, H7, Lu9 and P6. Small cylindrical magnets are preferred. The flat end of the cylinder magnet encounters the acupuncture point.

Typical Electrical Parameters

Human skin resistance can run from around 1000 Ohms to around 100 k Ohms depending on contact area, moisture and condition of the skin.

During stimulation mode the preferred pulses have the following output parameters at a skin impedance of 100 k Ohms:
Voltage 0-8.8 V Frequency 2.5 Hz DC Square wave (a square wave that is entirely of positive or negative voltage with respect to ground).

The pulse current varies with the intensity setting:
At the maximum intensity setting (applying 8.8 volts): the following currents result:
 100 k Ohms impedance gives 85-88 uA.
 10 k Ohms impedance would give 880 uA (unless current is further limited by the circuitry or power supply capability to 600 uA or less).

It is desirable to limit current for safety and for battery conservation. The preferred maximum current is 600 uA or less.

Minimum intensity (about 1 V applied) is between 6-8 uA.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A wrist-worn acupuncture stimulation device comprising:
 a watch-like case having a top side and bottom side;
 a wrist strap or band attachable to the watch-like case constructed to allow the case to be worn on a human wrist;
 three supply electrodes and a ground electrode, each of the three supply electrodes and the ground electrode being mounted on the bottom side of the case, the three supply electrodes electrically connected to a variable voltage power supply and located in positions corresponding to the H7, Lu9 and P6 acupuncture points, the three supply electrodes configured to inject current into the H7, Lu9 and P6 acupuncture points, the ground electrode configured to collect current from three electrodes after passing through the H7, Lu9 or P6 acupuncture points and return said current to the variable voltage power supply; and
 a first button, a second button and a third button mounted on the top side of the case, wherein the first button causes current to be injected into the H7 acupuncture point, the second button causes current to be injected into the Lu9 acupuncture point and the third button causes current to be injected into the P6 acupuncture point;
 wherein the current is a direct current (DC) or a plurality of direct current pulses; between 2.0 Hz to 3.0 Hz and
 wherein the variable voltage power supply produces a voltage output of amplitude of from 1.0 volts to 8.8 volts.

2. The wrist-worn acupuncture stimulation device of claim 1, wherein the current is injected into all three of the H7, Lu9 and H7 acupuncture points simultaneously when the first button and the second button and the third button are depressed simultaneously.

3. The wrist-worn acupuncture stimulation device of claim 2, further comprising three LEDs mounted on the top side of the case, each LED corresponding to one of the three buttons.

4. The wrist-worn acupuncture stimulation device of claim 1, further comprising a photoplethysmography (PPG) device configured to measure at least heart rate variability rate (HRV) and heart rate (HR).

5. The wrist-worn acupuncture stimulation device of claim 4, wherein upon the PPG device detecting a negative HRV level, the wrist-worn acupuncture stimulation device is activated for a set period of time.

6. The wrist-worn acupuncture stimulation device of claim 1, further comprising short-range communications with a mobile telephone, wherein the mobile telephone executes a stored application program utilizing said short-range communications.

7. The wrist-worn acupuncture stimulation device of claim 1, further comprising closed-loop control of said current.

8. The wrist-worn acupuncture stimulation device of claim 1, further comprising a display screen.

9. The wrist-worn acupuncture stimulation device of claim 1, further comprising a microcontroller in communication with the three supply electrodes and the ground electrode, wherein the microcontroller is configured to communicate bi-directionally via short-range communication with a telephone App.

10. A wrist-worn acupuncture stimulation device comprising:
 a watch-like case having a top side and bottom side;
 a wrist strap or band attachable to the watch-like case constructed to allow the case to be worn on a human wrist;

three supply electrodes and a ground electrode, each of the three supply electrodes and the ground electrode being mounted on the bottom side of the case, the three supply electrodes electrically connected to a variable voltage pulse power supply and located in positions corresponding to the H7, Lu9 and P6 acupuncture points, the three supply electrodes configured to inject current respectively into the H7, Lu9 and P6 acupuncture points, the ground electrode configured to collect current from any or all of the three electrodes after passing through the H7, Lu9 or P6 acupuncture points, and return said current to the variable voltage pulse power supply; and a first button, a second button, and a third button, wherein current is injected into all three of the H7, Lu9 and H7 acupuncture points simultaneously when the first button and the second button and the third button are depressed simultaneously;

wherein the current is a 2.0 Hz to 3.0 Hz direct current (DC) or a plurality of direct current pulses$_2$ and wherein the variable voltage pulse power supply produces a voltage output of amplitude of from 1.0 volts to 8.8 volts peak.

11. The wrist-worn acupuncture stimulation device of claim 10, wherein the pulse repetition rate is between 2 Hz and 3 Hz.

12. The wrist-worn acupuncture stimulation device of claim 10, wherein the current is a square wave.

13. The wrist-worn acupuncture stimulation device of claim 10, wherein the current is limited to 600 uA.

14. The wrist-worn acupuncture stimulation device of claim 10, further comprising a photoplethysmography (PPG) device configured to measure at least heart rate variability rate (HRV) and heart rate (HR), wherein upon the PPG device detecting a negative HRV level, the wrist-worn acupuncture stimulation device is activated for a set period of time.

15. The wrist-worn acupuncture stimulation device of claim 10, further comprising a microcontroller in communication with the three supply electrodes and the ground electrode, wherein the microcontroller is configured to communicate bi-directionally via short-range communication with a telephone App.

16. A wrist-worn acupuncture stimulation device comprising:

a watch-like case having a top side and bottom side;

a wrist strap or band attachable to the watch-like case constructed to allow the case to be worn on a human wrist;

three supply electrodes and a ground electrode, each of the three supply electrodes and the ground electrode being mounted on the bottom side of the case, the three supply electrodes electrically connected to a variable voltage pulse power supply and located in positions corresponding to the H7, Lu9 and P6 acupuncture points, the three supply electrodes configured to inject current respectively into H7, Lu9 and P6 acupuncture points, the ground electrode configured to collect current from any or all of the three electrodes after passing through the H7, Lu9 or P6 acupuncture points, and return said current to the variable voltage pulse power supply; and a first button, a second button, and a third button, wherein current is injected into two of the H7, Lu9 and H7 acupuncture points simultaneously when the first button and the second button or the second button and the third button or the first button and the third button are depressed simultaneously;

wherein the current is a 2.0 Hz to 3.0 Hz direct current (DC) or a plurality of direct current pulses, and wherein the variable voltage pulse power supply produces a voltage output of amplitude of from 1.0 volts to 8.8 volts peak.

17. The wrist-worn acupuncture stimulation device of claim 16, further comprising a photoplethysmography (PPG) device configured to measure at least heart rate variability rate (HRV) and heart rate (HR), wherein upon the PPG device detecting a negative HRV level, the wrist-worn acupuncture stimulation device is activated for a set period of time.

18. The wrist-worn acupuncture stimulation device of claim 16, further comprising a microcontroller in communication with the three supply electrodes and the ground electrode, wherein the microcontroller is configured to communicate bi-directionally via short-range communication with a telephone App.

* * * * *